(12) United States Patent
Nodin et al.

(10) Patent No.: US 9,440,229 B2
(45) Date of Patent: Sep. 13, 2016

(54) LEAKTIGHT JOINING DEVICE FOR THE ASEPTIC TRANSFER OF A BIOPHARMACEUTICAL PRODUCT BETWEEN A CHAMBER AND A CONTAINER

(75) Inventors: Gaelle Nodin, Saint Maximin la Sainte Baume (FR); Jeremy Gibelin, Le Beausset (FR)

(73) Assignee: SARTORIUS STEDIM FMT SAS, Aubagne (FR)

( * ) Notice: Subject to any disclaimer, the term of this patent is extended or adjusted under 35 U.S.C. 154(b) by 295 days.

(21) Appl. No.: 14/234,788

(22) PCT Filed: Jul. 12, 2012

(86) PCT No.: PCT/FR2012/051664
§ 371 (c)(1),
(2), (4) Date: Jan. 24, 2014

(87) PCT Pub. No.: WO2013/017765
PCT Pub. Date: Feb. 7, 2013

(65) Prior Publication Data
US 2014/0150924 A1 Jun. 5, 2014

(30) Foreign Application Priority Data
Jul. 29, 2011 (FR) .................................... 11 57007

(51) Int. Cl.
*B01L 1/02* (2006.01)
*G21F 7/005* (2006.01)
*C12M 1/12* (2006.01)

(52) U.S. Cl.
CPC ................. *B01L 1/02* (2013.01); *C12M 37/04* (2013.01); *G21F 7/005* (2013.01)

(58) Field of Classification Search
CPC ... G21F 7/005; B65B 61/06; B65B 69/0033; B01L 1/02

USPC ................. 141/383, 384, 98, 85, 329–330; 220/501; 414/412, 292, 212; 53/292, 53/133.3, 381.2
See application file for complete search history.

(56) References Cited

U.S. PATENT DOCUMENTS

| | | | |
|---|---|---|---|
| 5,853,207 A | 12/1998 | Saint Martin et al. | |
| 6,553,722 B1 | 4/2003 | Porret et al. | |
| 8,919,830 B2 * | 12/2014 | Norton | B01L 1/02 292/143 |

FOREIGN PATENT DOCUMENTS

| | | |
|---|---|---|
| EP | 0 688 020 A1 | 12/1995 |
| EP | 1 141 974 A1 | 5/2004 |

(Continued)

OTHER PUBLICATIONS

International Search Report, dated Oct. 15, 2012, from corresponding PCT application.

*Primary Examiner* — Mark A Laurenzi
*Assistant Examiner* — Timothy P Kelly
(74) *Attorney, Agent, or Firm* — Young & Thompson

(57) ABSTRACT

A leaktight joining device for ensuring the aseptic transfer of a biopharmaceutical product between a chamber equipped with a removable door and a container equipped with a removable cover, includes: stationary temporary flanging elements, stationary unlocking elements capable of changing the container from an initial locking position to an intermediate unlocking position so as to ensure an aseptic communication between the container and the chamber, stationary locking element capable of changing the container from the intermediate locking position to a final locking position, an annular functional ring gear capable of actuating the stationary unlocking elements and the stationary locking elements of the container. The stationary temporary flanging elements, the stationary unlocking elements, and the stationary locking elements are mechanically linked to the annular functional ring gear and arranged so that the unidirectional rotation of the annular functional ring gear about the geometric axis of rotation successively drives the actuation thereof.

23 Claims, 6 Drawing Sheets

(56) References Cited

FOREIGN PATENT DOCUMENTS

| | | |
|---|---|---|
| FR | 2 721 289 A | 12/1995 |
| FR | 2 872 446 A1 | 1/2006 |
| GB | 2 102 719 A | 2/1983 |
| GB | 2 218 663 A | 11/1989 |
| WO | 2010/054031 A1 | 5/2010 |

\* cited by examiner

LEAKTIGHT JOINING DEVICE FOR THE ASEPTIC TRANSFER OF A BIOPHARMACEUTICAL PRODUCT BETWEEN A CHAMBER AND A CONTAINER

BACKGROUND OF THE INVENTION

1. Field of the Invention

The invention relates to the field of the aseptic transfer of biopharmaceutical products between a container and a closed chamber.

More specifically, a first aspect of the invention concerns a leaktight joining device specially intended for the aseptic transfer of products belonging to the biopharmaceutical field, between a container and a closed chamber. The invention also relates, according to a second aspect, to an assembly comprising a container, such a leaktight joining device, and a chamber, in order to ensure the aseptic transfer of biopharmaceutical products between the container and the closed chamber. The invention further relates, in a third aspect, to a method for the aseptic transfer of a biopharmaceutical product between the container and the closed chamber.

2. Description of the Related Art

The term "biopharmaceutical product" or "biopharmacy product" is understood here to mean that which is related to biotechnology, pharmacy, and more generally to the medical field. In particular, a biopharmaceutical product is a product originating from biotechnology—culture media, cell cultures, buffer solutions, artificial nutrition liquids—or a product intended to be used in the pharmaceutical or medical field, at least in part, as a more or less finely divided solid, as a liquid, or as a paste, or, more generally, a physical product—cap, vessel, integrated ports or tube, syringe, syringe plunger, functional processing or packaging means, a more or less complex assembly comprising a plurality of products, etc.—intended for use inside the closed chamber.

By convention, the terms "container" or "containing" mean that which, in biopharmacy, is able to and is designed for containing, enclosing, or holding in its interior a specific biopharmaceutical content or where appropriate several biopharmaceutical contents, in a static manner that is more or less lasting or permanent. Such biopharmaceutical contents typically consist of one or more biopharmaceutical product(s) as defined above. Such containers may be rigid or flexible, reusable or disposable, of various sizes, for example bags, sleeves, containers, vessels, bioreactors, or spouts for biopharmaceutical use, this not being an exhaustive list.

In the field of aseptic transfers of biopharmaceutical products, there is a need for establishing a connection between a container and a sealed chamber in order to transfer biopharmaceutical products without breaking the seal of the chamber and/or container relative to the outside environment as this could result in contamination of the biopharmaceutical products.

To do this, the "Biosafe Monolever Port 110" is known from the prior art—according to the preamble of claim 1—which relates to a leaktight joining device for ensuring such an aseptic transfer. This joining device comprises stationary temporary clamping means formed by a first annular ring gear rotatable about a geometric axis and actuating, via the displacement of a pushbutton causing this first annular ring gear to rotate, axial clamping elements for holding the container against the door of the chamber. The joining device also comprises stationary locking and unlocking means, arranged on the wall of the chamber and allowing the container to transition from an initial locking position where a removable cover seals the container, to an intermediate unlocking position where the removable cover is detached from the container and is held against the door of the chamber to form a seal for the aseptic transfer of biopharmaceutical products. These stationary locking and unlocking means consist of a second annular ring gear, rotatable about a geometric axis of rotation coinciding with the geometrical axis of the first annular ring gear and movable by manipulation of a lever. The movement of the lever in one direction rotates the annular ring gear in this direction and thus unlocks the removable cover from the container, while the movement of the lever in the other direction rotates the annular ring gear in the opposite direction and thus once again locks the removable cover against the container.

Such a construction has several disadvantages. First, the operation of clamping the container against the door of the chamber, on the one hand, and the operations of locking and unlocking the removable cover on the container, on the other hand, are performed by different actuation means—the pushbutton and the lever—which are independent of each other, which implies additional manufacturing costs and does not follow the general trend of simplification of the joining device. Also, the manipulation of such a joining device, although relatively simple, can sometimes result in complications because the operator must first move the pushbutton to ensure the container is clamped against the door of the chamber, then must move the lever in a first direction to unlock the removable cover from the container, and finally must move the lever in another direction to lock the removable cover against the container once again. These three independent actions must be carried out successively and at irregular time intervals, which is not intuitive and may cause voluntary or involuntary operator errors. Seals may then be compromised, both within the chamber and the containers, contaminating the biopharmaceutical products. Furthermore, such a plurality of actuation means causes numerous difficulties in automating this type of joining device.

Also known are the prior art documents EP-A1-0688020 and EP-A1-1141974 relating to a technology similar to that described above but where the joining device does not have an annular ring gear. The stationary clamping means and stationary unlocking/locking means are therefore actuated differently and via mechanisms that are structurally and functionally independent of each other.

Besides the drawbacks mentioned above, this solution involves the manipulation of three independent levers for locking and unlocking the removable cover of the container, arranged on the periphery of the chamber door. This increases the risk of manipulation errors, as well as increasing the at-risk areas where loss of integrity is likely to occur within the closed chamber or container.

Also known, from prior art document WO-A1-2010/054031, is a leaktight joining device having stationary locking/unlocking means similar to those described for the above documents. However, this leaktight joining device is usable with containers having built-in locking/unlocking means positioned directly on the periphery of the annular flange. These built-in locking/unlocking means are formed by several parts which can be manipulated independently of each other and are reversibly movable from a position in which they are introduced only into the flange of the container—the removable cover then being free—to a position where they are introduced simultaneously into the flange of the container and into the removable cover—the latter then being held in position so as to seal the container.

Such an embodiment also has several disadvantages. Firstly, the presence of several pins for removably locking the cover on the container, which can be moved independently of each other, does not ensure optimum reliability concerning loss of integrity of the joining device. Instead there is a high probability that manipulation of these different pins. In the specific movements required for locking and unlocking the removable cover, will lead to human error likely to cause failure in the internal isolation of the container or chamber. Secondly, the use of such manually movable pins causes accelerated wear on the equipment which must therefore be replaced more regularly. Thirdly, it should be noted that, as above, automation of such a system is particularly complex and therefore costly.

Document WO2010/054031 discloses a container intended for the aseptic transfer of a product to a chamber. The container comprises an annular flange defining an opening, and a removable cover is provided.

Document FR 2872446 discloses a double-door leaktight transfer device for performing a leaktight transfer between a first sealed chamber, for example a containment cell, and a second sealed chamber, for example a transfer box, comprising two doors each equipped with means for locking it to a flange having a central opening and an actuator for actuating the locking means, the actuators being rotatably mounted in the doors and comprising a peephole.

GB 2 218 663 discloses a double-lidded system comprising a first cylindrical container, open at one end, a first lid for the first container, means defining a port for a second container, and a second lid for said port, the first container having a peripheral seal for sealing to the port and to the first lid, and the second lid having a peripheral seal for sealing to the port and to the first lid, wherein the first lid comprises a catch mechanism of a first rotary element for securing the first lid to the first container, the first container incorporating engagement means for cooperating with the catch mechanism of the first rotary element, the second lid incorporates a rotary drive shaft extending through it and means for rotating the shaft are provided, and a catch mechanism of the second rotary element which can be actuated by the shaft to secure the first lid to the second lid, the first lid comprising means with which the catch mechanism of the second rotary element can engage, the system lastly incorporating a clutch teeth mechanism with at least twenty teeth which are engaged when the first lid is adjacent to the second lid such that rotation of the shaft causes simultaneous rotation of the first and second rotary catch mechanisms.

GB 2,102,719 discloses a system for bringing hazardous materials in and out of an enclosure, such as a glovebox, through a port in a wall of the enclosure. The port is normally closed by a door which cooperates with a removable end closure on a container or the like when the latter is presented to and secured to the port. The container is secured in position at the port by means of a rotatable coupling ring. A locking device ensures that the door cannot be opened in the absence of a container at the port and also that the container cannot be removed from the port when the door is open. Instead of the container, a glove secured to a rigid sleeve may be used to allow the operator to perform a work function within the glovebox.

SUMMARY OF THE INVENTION

In this context, the aim of the invention is therefore to provide a leaktight joining device that is without at least one of the previously mentioned limitations.

The invention more particularly relates to such a leaktight joining device for ensuring the transfer of biopharmaceutical products while limiting the number of manipulations to be performed and limiting the risk of leakages that could be caused by manipulation errors.

For this purpose, the invention relates to a leaktight joining device intended for ensuring the aseptic transfer of a biopharmaceutical product between a chamber equipped with a removable door and a container equipped with a removable cover, comprising: stationary temporary clamping means able to keep the container clamped against the chamber so that the removable cover of said container is sealingly held against the door of said chamber; stationary unlocking means able to transition the container from an initial locking position where the removable cover seals the container to an intermediate unlocking position where the removable cover is disengaged from the container and is sealingly held against the door of the chamber so as to ensure an aseptic communication between said container and said chamber; stationary locking means able to transition the container from the intermediate unlocking position to a final locking position where said removable cover once again seals the container; an annular functional ring gear able to rotate about a geometric axis of rotation so as to actuate the stationary unlocking means and the stationary locking means of the container. More particularly, the invention is characterized in that the stationary temporary clamping means, stationary unlocking means, and stationary locking means are mechanically linked to the annular functional ring gear and are arranged so that the one-way rotation of said annular functional ring gear about the geometric axis of rotation successively causes the actuation of the stationary temporary clamping means which ensures that the container is held in position against the chamber, then the actuation of the stationary unlocking means which ensures the transition to the intermediate unlocking position of the container, then the actuation of the stationary locking mains of the container which ensures the transition to the final locking position of the container, and the actuation of the stationary temporary clamping means which ensures the release the container.

This embodiment has several advantages. First, the use of a one-way annular ring gear for successively activating the stationary temporary clamping means, the stationary unlocking means, and the stationary locking means, is simpler and facilitates the task of the operators considerably by making the actuation process more natural and intuitive, thereby limiting or even completely eliminating any deliberate or accidental manipulation errors. Moreover, with this simplification, it is also possible to consider automating the aseptic transfer between the chamber and the container with no need to impose dependencies between numerous elements. In addition, the operation of assembling the joining device to the chamber is also simplified because, unlike the embodiments of the prior art, this solution groups most of the mechanical stresses in a single part, the annular ring gear, which avoids the need to manage the corresponding clearances when mounting the leaktight joining device on the chamber.

In one embodiment, the leaktight joining device further comprises stationary retention/release means able to disable/enable the opening of the chamber door and mechanically linked to the annular functional ring gear such that the one-way rotation of the annular functional ring gear about the geometric axis of rotation successively causes the actuation of the stationary temporary clamping means to ensure that the container is held in position against the chamber, then simultaneously or successively the actuation of the stationary unlocking means which ensures the transition to the intermediate unlocking position of the container and the actuation of the stationary retention/release means which ensures the release of the removable door of the chamber, then the actuation of the stationary locking means which ensures the transition to the final locking position of the container, then simultaneously or successively the actuation of the stationary retention/release means which ensures the retention of the removable door of the chamber and the actuation of the stationary locking means which ensures the transition to the final locking position of the chamber, then the actuation of the stationary temporary clamping means which ensures the release of the container relative to the chamber. The issues of loss of integrity are further improved when the stationary retention/release means are also actuated by unilateral movement of the annular ring gear. In effect, having such a mechanical connection between the annular functional ring gear and these stationary retention/release means ensures that the removable door is closed against the chamber opening when the leaktight joining device is not in the initial or final locking configuration of the container.

In this case, according to one embodiment, the stationary retention/release means comprise at least one stationary functional arrangement for retention/release formed by a functional ring portion forming gear teeth and a retention member able to engage with the functional ring portion forming gear teeth such that, during the one-way rotation of the annular functional ring gear, the retention member moves from a retention position where a covering portion prevents the door of the chamber from opening, to a release position where the covering portion no longer prevents the chamber door from opening. The use of a covering portion mechanically driven by the annular ring gear adds a safety measure to the retention of the chamber door while avoiding issues with dependencies or operational factors (sensors, actuators, PLCs, etc.) that could cause failures.

In one embodiment, the stationary unlocking means comprise at least one stationary functional unlocking arrangement formed by a functional ring portion forming an inward- and/or outward-facing radial cam and a radially movable pushing element cooperating with the functional ring portion forming a radial cam such that, during the one-way rotation of the annular functional ring gear to an intermediate unlocking position, the pushing element is moved and causes the container to transition from the initial locking position to the intermediate unlocking position. The use of a functional ring gear forming an inward- or outward-facing radial cam arranged on the ring simplifies management of the sizing, movements, and timed actuation of the stationary initial locking means. In addition, the use of pushbutton elements combined with this radial cam system provides a reliable and accurate solution with a small footprint.

In one embodiment, the stationary locking means comprise at least one stationary functional locking arrangement formed by a functional ring portion forming an inward- and/or outward-facing radial cam, and a radially movable pushing element cooperating with the functional ring portion forming a radial cam such that, during the one-way rotation of the annular functional ring gear to a final locking position, the pushing element is moved and causes the removable cover of the container to transition from the intermediate unlocking position to the final locking position. Similarly to the above, the functional ring gear forming an inward- or outward-facing radial cam simplifies the timed actuation of the stationary unlocking means and facilitates management of the sizing and movements of the stationary final locking means.

In this case, according to one embodiment, the functional ring portion forming a radial cam of the stationary locking and/or unlocking means is formed by a guideway arranged in the annular functional ring gear, and the radially movable pushing element of said stationary locking and/or unlocking means comprises a roller arranged in the guideway so that rotation of the annular functional ring gear generates a radial movement of the roller which causes the corresponding movement of an activation pin.

The use of a guideway associated with a roller is simple to manufacture and also ensures movement that is accurate, reliable, and small in footprint.

In this case, according to one embodiment, the stationary functional unlocking arrangement and the stationary functional locking arrangement are composed of the same radially movable pushing element.

More particularly, in one embodiment, the functional ring portion forming a radial cam of the stationary functional locking arrangement is arranged in the extension of the functional ring portion forming a radial cam of the stationary functional unlocking arrangement, considering the one-way direction of rotation of the annular functional ring gear.

In this case, according to one embodiment, the ring portions forming a radial cam of the stationary functional locking arrangement and of the stationary functional unlocking arrangement are formed by a continuous guideway arranged in the annular functional ring gear, and the radially movable pushing element comprises a roller arranged in the continuous guideway such that the rotation of the annular functional ring gear generates radial movement of the roller which results in the corresponding displacement of an activation pin. The use of a pushing element that is set in motion by a single roller placed in a single continuous guideway for operating two stationary functional locking and unlocking arrangements is a simple and naturally economical solution that also reduces the risk of premature wear to the system and the risk of production errors.

In an alternative embodiment, the stationary unlocking means and the stationary locking means can be structurally and functionally separate and independent of each other.

In one embodiment, the stationary temporary clamping means comprise at least one stationary functional arrangement for temporary clamping implemented based on a functional clamping ring portion having, on the one hand, a functional surface for axial clamping and, on the other hand, an insertion opening for built-in complementary clamping means arranged on a portion of the outer periphery of the container. As above, the use of a functional ring portion to maintain the container in the axial position allows limiting production costs by avoiding the use of a separate part from the annular functional ring gear. Furthermore, this solution with its functional surface for axial clamping and its insertion opening allows indexing the position of the container at the time of its placement against the leaktight joining device. In addition, this solution provides an added level of security: as the functional clamping ring portion is mechanically linked to the stationary locking and unlocking means, it is impossible for the flange of the container to be released prematurely.

In this case, according to one embodiment, the functional clamping ring portion is implemented on an inner peripheral edge of the annular functional ring gear.

According to one embodiment, the leaktight joining device also comprises stationary operating means for the chamber door, able to open the chamber door and seal it closed.

In this case, according to one embodiment, the stationary operating means for the chamber door are mechanically driven by the annular functional ring gear. The mechanical association of the stationary operating means for the chamber door on the annular functional ring gear ensures the timed actuation of the door and simplifies the leaktight joining device, for the same reasons as above.

For the above case, in an alternative embodiment, the stationary operating means for the chamber door are driven by a motor controlled by the movements of the annular functional ring gear.

According to one embodiment where the leaktight joining device comprises stationary operating means, it is possible that these means are adapted to move the door first in an axial direction, then in a direction substantially perpendicular to the axial direction so that the door does not obstruct the passage of the biopharmaceutical product. In this way, the chamber door, once opened, does not interfere with access to the container.

In one embodiment, the annular functional ring gear, the stationary temporary clamping means of the container, the stationary unlocking means of the container, and the stationary locking means of the container are positioned outside the chamber. Such placement of these elements outside the chamber simplifies the installation and repair operations, since these operations do not occur within the sealed environment inside the chamber but are instead done from the outside.

In this case, according to one embodiment, firstly the functional ring portion forming gear teeth of the stationary functional arrangement for retention/release is positioned outside the chamber, secondly the retention member of said stationary functional arrangement for retention/release is positioned inside the chamber, and thirdly said retention member is driven by a drive shaft which passes through the peripheral wall of the chamber.

In one embodiment, the stationary temporary clamping means of the container, the stationary unlocking means of the container, and the stationary locking means of the container respectively comprise n stationary functional arrangement(s) for temporary clamping, n stationary functional unlocking arrangement(s), n stationary functional locking arrangement(s), with n greater than or equal to 1, so that with each rotational movement of the annular functional ring gear in the one-way direction corresponding to 1/n complete revolutions there is the corresponding successive actuation of the stationary temporary clamping means of the container to hold the container in position against the chamber, of the stationary unlocking means of the container to ensure the transition to the intermediate unlocking position of the container, of the stationary locking means of the container to ensure the transition to the final locking position of the container, and of the stationary temporary clamping means of the container to ensure the release of said container. The fact that a plurality of functional arrangements are distributed on the annular functional ring gear allows completing multiple aseptic transfer cycles with one complete rotation and therefore limits the speed of rotation of the annular functional ring gear while favoring precision. Furthermore, given the relative positioning of these functional arrangements, they are indexed with respect to each other so that the container can be placed in multiple positions without posing difficulties for the aseptic transfer process.

In this case, according to one embodiment, n may be 3 or 4.

A second aspect of the invention relates to an assembly comprising a chamber and a leaktight joining device specially intended for association with a single-use container equipped with a removable cover in order to perform the aseptic transfer of a biopharmaceutical product between the chamber and the container, wherein the chamber comprises a peripheral wall having an opening that is sealed by a removable door, and wherein the leaktight joining device is as described above.

In this case, according to one embodiment, the assembly further comprises a single-use container equipped with a removable cover.

In this case, according to one embodiment, the single-use container is specially intended for the transport and the aseptic transfer of a product belonging to the biopharmaceutical field, and comprises: an annular flange delimiting an opening; a removable cover adapted for sealing the opening of the annular flange; built-in means for locking/unlocking the removable cover on the annular flange; and a peripheral envelope integral with the annular flange and delimiting an enclosed inside space adapted for receiving products belonging to the biopharmaceutical field. The built-in locking/unlocking means comprise at least one built-in functional locking/unlocking arrangement formed, on the one hand, by a through-housing formed in the annular flange and a blind housing formed in the removable cover and in the extension of the through-housing when the removable cover seals the opening of the annular flange, and, on the other hand, by a pin at an inner radial position and a pin at an outer radial position both capable of being introduced and moved within the blind housing of the removable cover and the through-housing of the annular flange. Furthermore, the container is able to be in an initial locking position where, on the one hand, the pin at an inner radial position has a functional locking portion arranged in the blind housing of the removable cover and a functional locking portion arranged in the through-housing of the annular flange so as to prevent the relative movement of the removable cover with respect to the annular flange, and, on the other hand, the pin at an outer radial position is at least partially arranged in the through-housing of the annular flange; the container is also able to be in an intermediate unlocking position where, on the one hand, the pin at an inner radial position is at least partially arranged in the blind housing of the removable cover and is completely outside the through-housing of the annular flange, and, on the other hand, the pin at an outer radial position is at least partially arranged in the through-housing of the annular flange and is completely outside the blind housing of the removable cover so as to allow the relative movement of the removable cover with respect to the annular flange; and the container is further able to be in a final locking position where, on the one hand, the pin at an inner radial position is arranged in the blind housing of the removable cover, and, on the other hand, the pin at an outer radial position has an internal functional portion for final locking arranged in the blind housing of the removable cover and an external functional portion for final locking arranged in the through-housing of the annular flange so as to prevent the relative movement of the removable cover with respect to the annular flange.

A third aspect of the invention relates to a method of aseptic transfer, intended to ensure the aseptic transfer of a biopharmaceutical product between a container and a chamber which are part of an assembly as described above, the method comprising successive steps consisting of: having available the chamber, the leaktight joining device, and the container; positioning the container against the peripheral wall of the chamber; generating an axial clamping of the annular flange of the container against the peripheral wall of the chamber by one-way rotation of the annular functional ring gear; generating the transition of the container from the initial locking position to the intermediate unlocking position by one-way rotation of the annular functional ring gear; simultaneously opening the removable door of the chamber and the removable cover of the container, the removable cover being sealingly attached against the removable door; aseptically transferring one or more biopharmaceutical product(s) between the container and the chamber; simultaneously closing the removable door of the chamber and the removable cover of the container, the removable cover being sealingly attached against the removable door; generating the transition of the container from the intermediate unlocking position to the final locking position by one-way rotation of the annular functional ring gear; generating the axial unclamping of the annular flange of the container relative to the peripheral wall of the chamber by one-way rotation of the annular functional ring gear.

BRIEF DESCRIPTION OF THE DRAWING FIGURES

Other features and advantages of the invention will become apparent from the description which is provided below for informational purposes and which is non-limiting, with reference to the accompanying drawings, where:

DETAILED DESCRIPTION OF THE INVENTION

Figure 1:
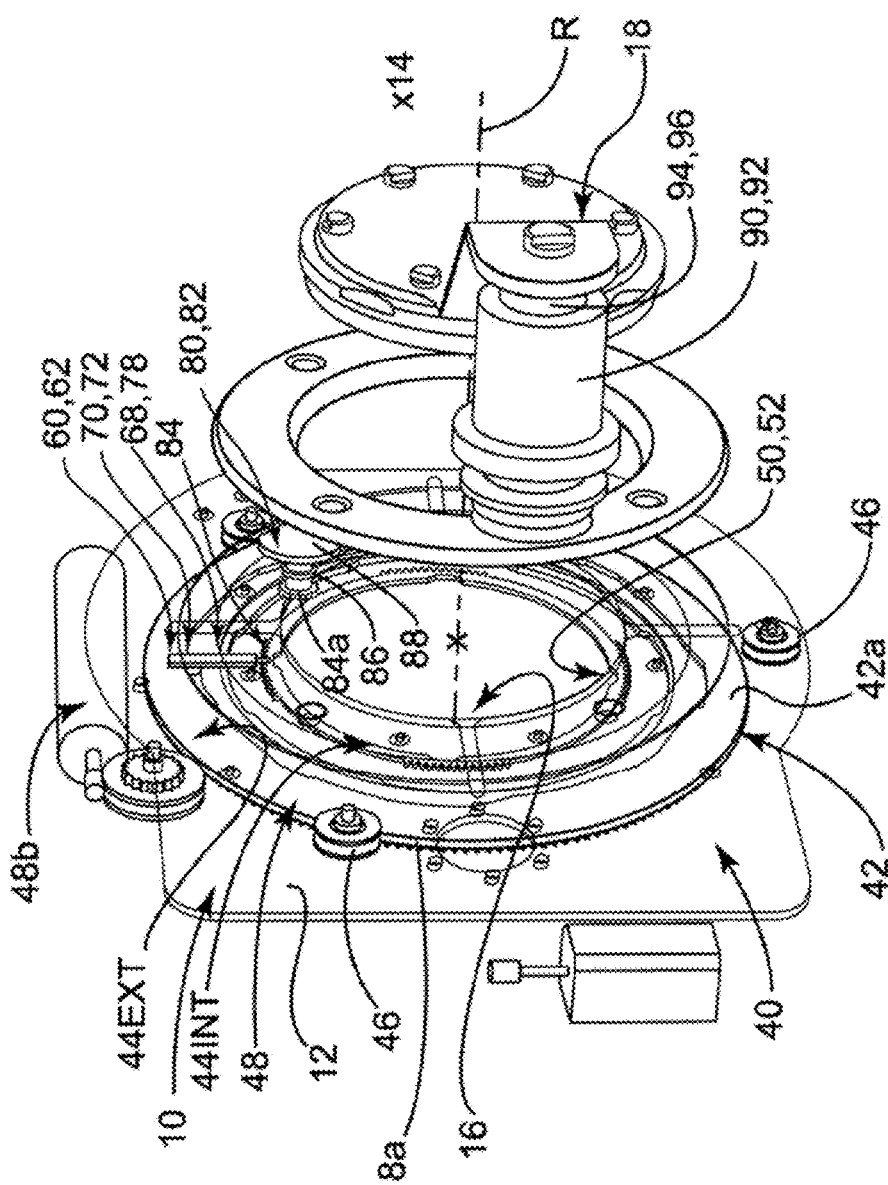
FIG. 1 is a general overview, showing an exploded perspective view of an embodiment of a leaktight joining device associated with the peripheral wall of a chamber.

FIG. 1 shows a closed chamber 10 comprising a peripheral wall 12 defining an enclosed inside space 14 and a circular opening 16 allowing the introduction of biopharmaceutical products (not shown) into the enclosed inside space 14.

The chamber 10—which can be an enclosed area or other analogous system—is designed to be permanently isolated from the outside environment. Thus, to avoid any loss of integrity and to maintain an aseptic environment within the inside space 14, the annular opening 16 is hermetically sealed by a removable door 18 positioned in the inside space and able to move from a closed position where the circular opening 16 is obstructed to an open position where the circular opening 16 is no longer obstructed.

By convention, the terms "internal" and "external" or "inner" and "outer" are used in the rest of this document to describe the relative positions of objects with respect to the geometric axis of the annular opening 16. Thus, objects described as "internal" or having an "inner radial position" should be regarded as positioned closest to the geometric axis of the annular opening 16, while objects described as "external" or having an "outer radial position" is to be considered as positioned farthest from the geometric axis of the annular opening 16.

Figure 2A:
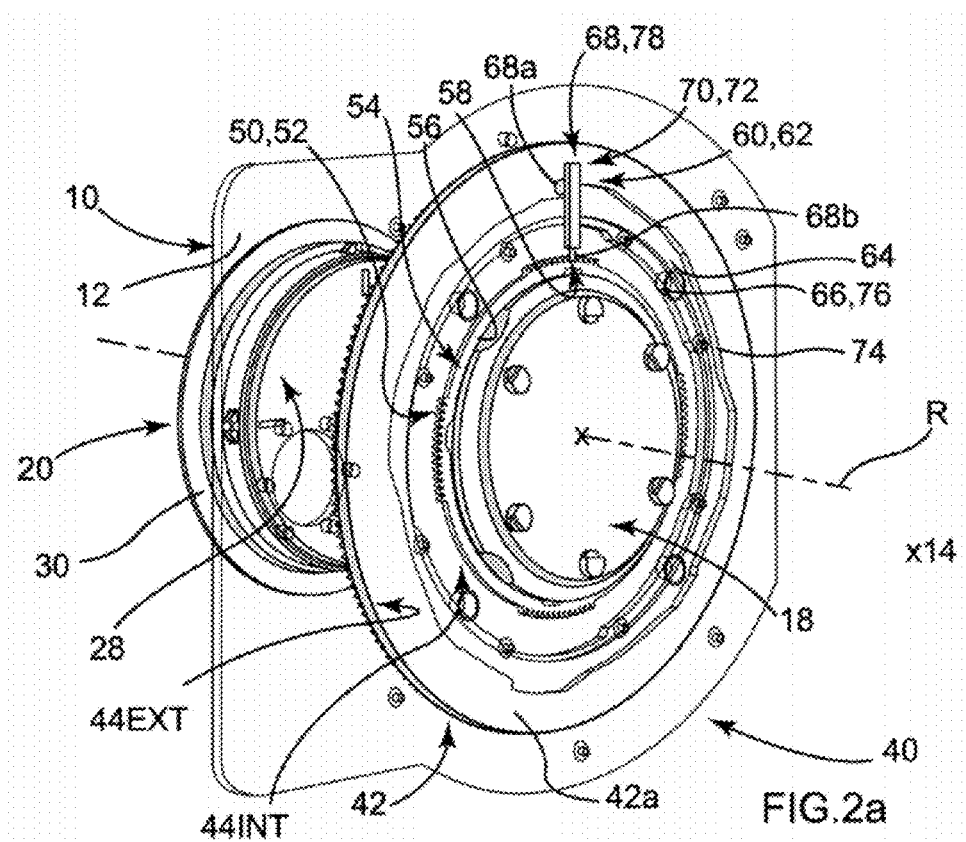
FIGS. 2a and 2b are two general perspective views, from inside the chamber and from outside the chamber, of the leaktight joining device of FIG. 1 installed on a portion of the peripheral wall of the chamber and ready to be associated with the annular flange of a container according to the invention.
Figure 2B:
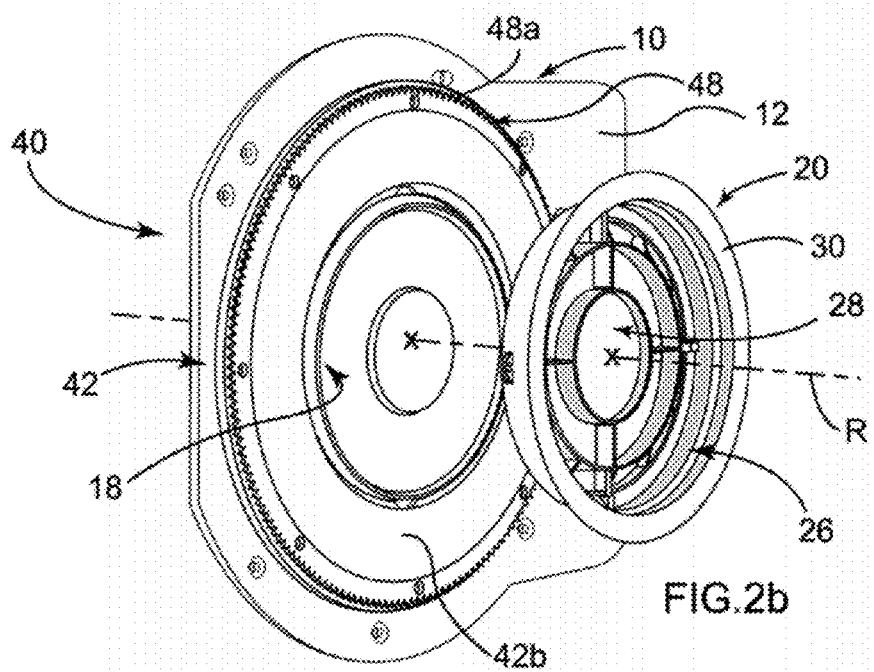

FIGS. 2a and 2b show a container 20 intended for transporting biopharmaceutical products and ready to be associated with the closed chamber 10 in order to perform an aseptic transfer of biopharmaceutical products to or from this chamber 10.

For this purpose, the container 20 comprises a peripheral envelope (not shown) defining an enclosed inside space 24 into which the biopharmaceutical products can be introduced. The peripheral envelope also comprises an annular opening 26 delimited by an annular flange 30 to which the peripheral envelope is integrally attached. The container 20 further comprises a removable cover 28 capable of sealing the opening 24 of the annular flange 30 by resting on a seal 22.

The container 20 can be realized according to different embodiments, and therefore can have a peripheral envelope that is flexible and intended for a single use or is rigid and intended to be reused after a decontamination procedure well known to those skilled in the art.

FIGS. 1, 2a, and 2b illustrate an embodiment of a leaktight joining device 40.

This leaktight joining device 40 is intended to allow the aseptic transfer of biopharmaceutical products from the container 20 (described below) to the chamber 10. The object of the leaktight joining device 40 is therefore firstly to allow the assembly of the chamber 10 and the container 20, and then to allow placing the inside space 14 of this chamber 10 in temporary communication with the inside space of this container 20 in order to transfer biopharmaceutical products from one to the other, and lastly, to ensure the separation of said chamber 10 and said container 20.

These successive steps—encompassed below under the descriptor "aseptic transfer"—must be carried out without any communication between the outside environment and the inside spaces 14, 24 of the chamber 10 and of the container 20.

To achieve this, the leaktight joining device 40 according to the embodiment of FIG. 1 has a part formed outside the chamber 10 and supported by the peripheral wall 12—or by a supporting part distinct from the peripheral wall 12 but immovably attached to it—facing the annular opening 16. More specifically, the leaktight joining device 40 comprises an annular functional ring gear 42 having a face 42a oriented towards the peripheral wall 12 of the chamber 10 and a face 42b oriented towards the outside environment.

The annular functional ring gear 42 also has an inner peripheral edge $44_{INT}$ and an outer peripheral edge $44_{EXT}$ inscribed within three track rollers 46 which are supported by the external face of the peripheral wall 12. The annular functional ring gear 42 is thus positioned outside the chamber 10, which facilitates any maintenance operations. The three track rollers 46 form a track for the annular functional ring gear, and allow it to rotate about the geometric axis of the annular opening 16. It should be stressed, however, that the position of the annular functional ring gear could be maintained by some other similar mechanical element (bearing, etc.).

In the embodiment of FIG. 1, the annular functional ring gear 42, which presents several portions having different mechanical functions (described later) is formed as a single part—by machining, molding, or similar—from a single block of material. This embodiment has the advantage of simplifying the production of the annular functional ring gear, while simultaneously reducing the production costs and ensuring optimal positioning of the functional surfaces of the annular functional ring gear 42. However, it is understood that in other embodiments the annular functional ring gear may be formed from a plurality of discrete mechanical parts assembled together into one piece such that rotation of one of these mechanical parts about the geometric axis of rotation R causes the rotation of the whole.

It should be noted that, by convention, objects referred to as "stationary" are part of the leaktight joining device 40 and are therefore intended to be connected and permanently attached to the chamber 10. Conversely, objects referred to as "built-in" are intended to be supported by the containers 20 and therefore move with said containers.

Figure 3A:
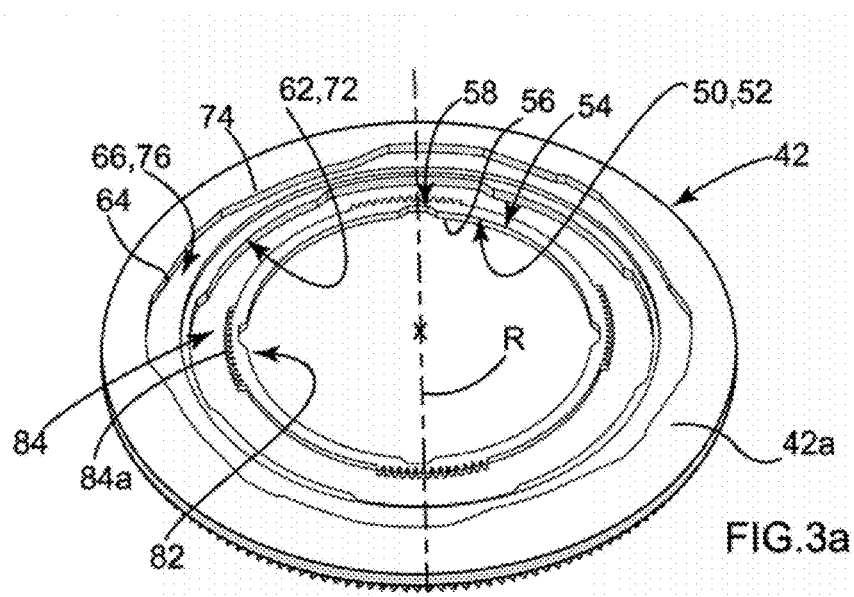
FIGS. 3a and 3b are two perspective detail views of the annular functional ring gear as part of the embodiment of the joining device of FIG. 1.
Figure 3B:
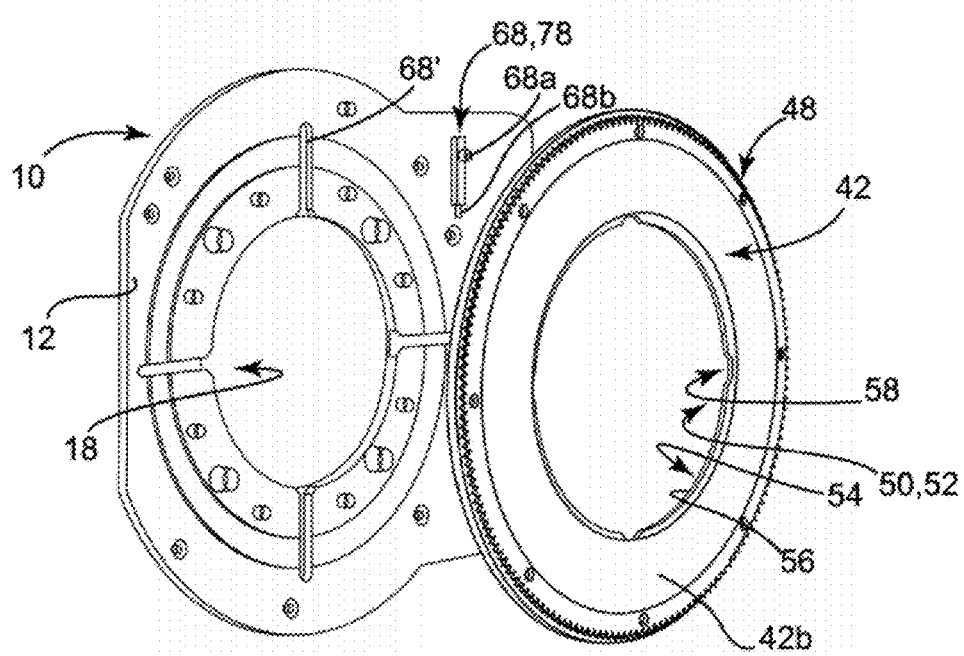

The annular functional ring gear 42, more particularly illustrated in FIGS. 3a and 3b, has a stationary rotary drive portion 48 arranged near the outer peripheral edge of the annular functional ring gear 42 and formed by radially oriented teeth 48a driven by a motor 48b placed outside the chamber 10, or in an alternative embodiment, by a manually actuated lever (not shown). From the momentum of the motor 48b, the annular functional ring gear is able to begin a one-way rotation about the geometric axis of rotation R. By convention, the one-way rotation will be considered below to be clockwise. However, the direction of rotation of the annular functional ring gear can alternatively correspond to the counterclockwise direction.

The leaktight joining device 40 comprises stationary temporary clamping means 50.

The stationary temporary clamping means 50 serve to keep the container 20 clamped against the chamber 10 so that the removable cover 28 of the container 20 is sealingly applied against the removable door 18 of the chamber 10.

These stationary temporary clamping means 50 are mechanically linked to the annular functional ring gear 42 so that the clockwise rotation of this annular functional ring gear 42 about the geometric axis of rotation R mechanically actuates the stationary temporary clamping means 50.

In the embodiment of FIG. 1, the stationary temporary clamping means 50 comprise four stationary functional arrangements for temporary clamping 52 regularly distributed around the annular functional ring gear 42. Each of these stationary functional arrangements for temporary clamping 52 is formed of a functional clamping ring portion 54 which is part of the annular functional ring gear 42. Each functional clamping ring portion 54 thus has a functional surface for axial clamping 56, and an insertion opening 58 for built-in complementary clamping means arranged on a portion of the outer periphery of the container (described below).

In the embodiment of FIG. 1, the functional surface for axial clamping 56 is formed on the inner peripheral edge 44$_{INT}$ of the annular functional ring gear 42 by an axially offset extension of the outer face of the peripheral wall 12 of the chamber 10, with regular interruptions forming the insertion opening 58. However, alternative embodiments for axially clamping the annular flange 30 of the container 20 against the outer face of the peripheral wall 12 of the chamber 10 could also be considered.

The leaktight joining device 40 comprises stationary unlocking means 60.

The stationary unlocking means 60 are intended for allowing the container 20 to transition from an initial locking position where the removable cover 28 seals the container 20, to an intermediate unlocking position where the removable cover 28 is detached from the container and sealingly applied against the door 18 of the chamber 10 so as to ensure an aseptic communication between the container 20 and the chamber 10.

As before, these stationary unlocking means 60 are mechanically linked to the annular functional ring gear 42 so that the clockwise rotation of this annular functional ring gear 42 about the geometric axis of rotation R mechanically actuates the unlocking means 60. However, in view of the arrangement of these stationary unlocking means 60 relative to the stationary temporary clamping means 50, the actuation of the stationary unlocking means 60 only occurs after the axial clamping of the container 20 against the chamber 10.

In the embodiment of FIG. 1, also visible in FIGS. 3a and 3b, the stationary unlocking means 60 comprise several stationary functional unlocking arrangements 62—in this case four arrangements—regularly distributed around the annular functional ring gear 42.

Each of these stationary functional unlocking arrangements 62 firstly comprises a functional ring portion forming an inward- and/or outward-facing radial cam 64 which is part of the annular functional ring gear 42. In this case, the functional ring portion forming a radial cam 64 is realized based on a guideway 66 created in the annular functional ring gear 42 although this embodiment is not limiting.

Each of these stationary functional unlocking arrangements 62 secondly comprises a radially movable pushing element 68 able to cooperate with the functional ring portion forming a radial cam 64. In this manner, during the rotation of the functional ring gear 42 to an intermediate unlocking position, the relative movement of the annular functional ring gear 42 with respect to the pushing element 68—which remains rotationally fixed as it is locked in a complementary arrangement 68'—causes movement of said pushing element 68 in the radial direction and causes the container 20 to transition from an initial locking position to an intermediate unlocking position (described below).

More particularly, according to the illustrative and non-limiting embodiment of FIG. 1, the pushing element 68, which is rotationally fixed relative to the peripheral wall 12 of the chamber 10, comprises a roller 68a arranged in the guideway 66 and an activation pin 68b connected to the roller 68a so that the movement of this roller in the radial direction causes a radial movement of the activation pin 68b, until the container 20 transitions to the intermediate unlocking position.

It should be noted that the above phrase "movement in the radial direction" should be understood in its most general sense and can thus correspond to a direction passing through the geometric axis of rotation R or slightly inclined and forming an angle $\alpha$ relative to the radial direction of the annular flange 30.

The leaktight joining device 40 comprises stationary locking means 70.

The stationary locking means 70 are intended for causing the container 20 to transition from the intermediate unlocking position to a final locking position where said removable cover 28 once again seals the container 20.

As before, these stationary locking means 70 are mechanically linked to the annular functional ring gear 42 so that the clockwise rotation of this annular functional ring gear 42 about the geometric axis of rotation R mechanically actuates the stationary locking means 70. Similarly to the above, the relative position of the stationary locking means 70 and the stationary unlocking means 60 around the annular functional ring gear 42 is such that the actuation of these stationary locking means 70 can only occur after the stationary unlocking means 60 are stopped.

In the embodiment of FIG. 1, visible in FIGS. 3a and 3b, the stationary locking means 70 comprise four stationary functional unlocking arrangements 72 regularly distributed around the annular functional ring gear 42.

Each of these stationary functional unlocking arrangements 72 firstly includes a functional ring portion forming an inward- and/or outward-facing radial cam 74 which is part of the annular functional ring gear 42. As described above, this functional ring portion forming a radial cam 74 is based on a guideway 76 created in the annular functional ring gear 42, although this embodiment is not limiting.

Each of these stationary functional unlocking arrangements 72 then comprises a radially movable pushing element 78 able to cooperate with the functional ring portion forming a radial cam 74. In this manner, when the functional ring gear 42 is rotated to a final locking position, the relative movement of the annular functional ring gear 42 with respect to the pushing element 78—which remains rotationally fixed because it is retained in a complementary arrangement 68'—causes said pushing element 78 to be moved in the radial direction and causes the container 20 to transition from the intermediate unlocking position to a final locking position (described below).

More particularly, according to the illustrative and non-limiting embodiment of FIG. 1, the pushing element 78, which is rotationally fixed relative to the peripheral wall 12 of the chamber 10, is the same as the pushing element 68 which is part of stationary functional unlocking means 60. This pushing element 78 therefore comprises a roller 68a arranged in the guideway 76 and an activation pin 68b connected to the roller 68a so that the movement of said roller in the radial direction causes a radial movement of the activation pin 68b, until the container 20 transitions to the intermediate unlocking position.

It therefore follows that the functional ring portion forming a radial cam 74 of the stationary functional locking arrangement 72 is arranged in the extension of the functional ring portion forming a radial cam 64 of the stationary functional unlocking arrangement 62, considering the one-way rotation of the annular functional ring gear 42. In this regard, the ring portions forming a radial cam 72, 62 of the stationary functional locking arrangement 74 and of the stationary functional unlocking arrangement 62 are formed by a continuous guideway 66, 76 arranged in the annular functional ring gear 42, and the radially movable pushing element 68, 78 comprises a roller 68a arranged in the continuous guideway 66, 76 such that the rotation of the annular functional ring gear generates radial movement of the roller 68a which results in the corresponding displacement of an activation pin 38b.

Conversely, in an alternative embodiment (not shown), the stationary unlocking means 60 and the stationary locking means 70 may optionally be structurally and functionally distinct and independent of each other.

The leaktight joining device 40 comprises stationary retention/release means 80.

These stationary retention/release means 80 are intended to disable/enable the opening of the removable door 18 of the chamber 10 and are mechanically connected to the annular functional ring gear 42 such that the clockwise one-way rotation of this annular functional ring gear 42 about the geometric axis of rotation R mechanically actuates the stationary retention/release means 80. More particularly, because of the position of these stationary retention/release means 80 on the annular functional ring gear 42, these means ensure the release of the removable door 18 of the chamber 10. In the embodiment of FIG. 1, the stationary retention/release means 80 ensure the release of the removable door 18 after actuation of the stationary unlocking means 60 has caused the container 20 to transition to the intermediate unlocking position. In this manner, the opening of the removable door 18 of the chamber 10 is delayed indefinitely when a problem occurs during the intermediate unlocking of the container 20. This minimizes containment issues—which are necessarily more complex to rectify within the chamber 10—which could result from improper handling of the container 20. Similarly, these stationary retention/release means 80 are arranged on the annular functional ring gear 42 to ensure that the removable door 18 of the chamber 10 remains in place until the stationary locking means 70 have been activated in order to transition the container 20 to the final locking position.

According to another embodiment, it would be equally possible to arrange the retention/release means 80 on the annular functional ring gear 42 so that said means release the removable door 18 simultaneously with the container 20 changing to the intermediate unlocking position, then block this removable door 18 simultaneously with the container 20 changing to the final locking position.

Finally, according to a third embodiment, it is possible to arrange the stationary retention/release means 80 on the annular functional ring gear 42 so that said means release the removable door 18 of the chamber 10 before the container 20 transitions to the intermediate unlocking position, and block the removable door 18 of the chamber 10 after the container 20 transitions to the final locking position.

The stationary retention/release means 80 as illustrated in FIG. 1 comprises at least one stationary functional arrangement for retention/release 82 formed by a functional ring portion forming gear teeth 84 which is part of the annular functional ring gear 42. As such, this functional ring portion forming gear teeth 84 is positioned outside the chamber 10.

Furthermore, according to the embodiment of FIG. 1, this functional ring portion forming gear teeth 84 is notched so as to engage with a drive shaft 86 passing through the peripheral wall 12 of the chamber 10 and which drives a retention member 88 during the one-way rotation of the functional ring gear. More particularly, the retention member 88—which is located within the inside space 14 of the chamber 10—is arranged to be able to move from a retained position where a covering portion 88a prevents the removable door 18 of the chamber 10 from opening, to a released position where the covering portion 88a no longer prevents the removable door 18 from opening.

The leaktight joining device 40 also comprises stationary operating means 90.

These stationary operating means 90 are intended for opening the removable door 18 of the chamber 10 and for sealing it closed again.

To do this, the stationary operating means 90 may, according to a first embodiment (not shown), be driven mechanically by the annular functional ring gear 42. In this case, the stationary operating means 90 are mechanically connected to the annular functional ring gear 42 so that the clockwise one-way rotation of this annular functional ring gear 42 about the geometric axis of rotation R mechanically actuates the stationary operating means 90. More particularly, the position of these stationary operating means 90 on the annular functional ring gear 42 allows opening the removable door 18 of the chamber 10 after the container 20 transitions to the unlocking position, then closing the removable door 18 before the container 20 transitions to the final locking position.

In a second embodiment illustrated by FIG. 1, the stationary operating means 90 are driven by a motor 92 controlled by the movement of the annular functional ring gear 42.

These stationary operating means 90 then comprise a rotational arm 94 adapted to rotate about a horizontal axis of rotation as well as a translational arm 96 able to move along a horizontal axis. In this manner, the stationary operating means 90 allow, by means of the motor 92, moving the removable door 18 of the chamber 10, first in an axial direction, then in a direction substantially perpendicular to the axial direction, so that the removable door 18 does not interfere with the passage of the biopharmaceutical product during the aseptic transfer between the chamber 10 and the container 20.

It should be noted that, according to the invention, the stationary temporary clamping means 50, the stationary unlocking means 60, the stationary locking means 70, and if appropriate the retention/release means 80 and the operating means 90, are mechanically linked to the annular functional ring gear 42 and arranged so that the clockwise one-way rotation of said annular functional ring gear 42 about the geometric axis of rotation R successively causes the actuation of the stationary temporary clamping means 50 to maintain the container 20 in position against the chamber 10, and then simultaneously or successively the actuation of the stationary unlocking means 60 which ensures that the container 20 transitions to the intermediate unlocking position and the actuation of the stationary retention/release means 80 which ensures the release of the removable door 18 of the chamber 10, then simultaneously or successively the actuation of the stationary retention/release means 80 which ensures the retention of the removable door 18 of the chamber 10 and the actuation of the stationary locking means 70 which ensures that the container 20 transitions to the final locking position, and once again the actuation of the stationary temporary clamping means 50 of the container in order to release the container 20.

Moreover, the stationary temporary clamping means 40 are arranged to ensure the positioning of the container 20 and an indexing relative to the other functional means. Similarly, the accumulation of multiple functional arrangements on the annular functional ring gear 42 allows completing a container 20 manipulation cycle with only 1/n of a revolution. In this current case, the embodiment comprises four distinct functional arrangements distributed regularly over the annular functional ring gear but it would be possible to include less—one, two, or three—or to include more.

It should be noted that the one-way rotation of the annular functional ring gear 42 actuates the stationary temporary clamping means, unlocking means, locking means, retention/release means, and operating means, which this annular functional ring gear moves in one direction of rotation or in the other.

It would also be possible to integrate this annular functional ring gear 42, not outside the chamber 10 as shown in the embodiment of FIG. 1 but directly in the inside space 14 of the chamber 10, against the inner face of the peripheral wall 12. This embodiment would avoid the use of retention/release means 80 having a drive shaft 86 passing through the peripheral wall 12.

Figure 4:
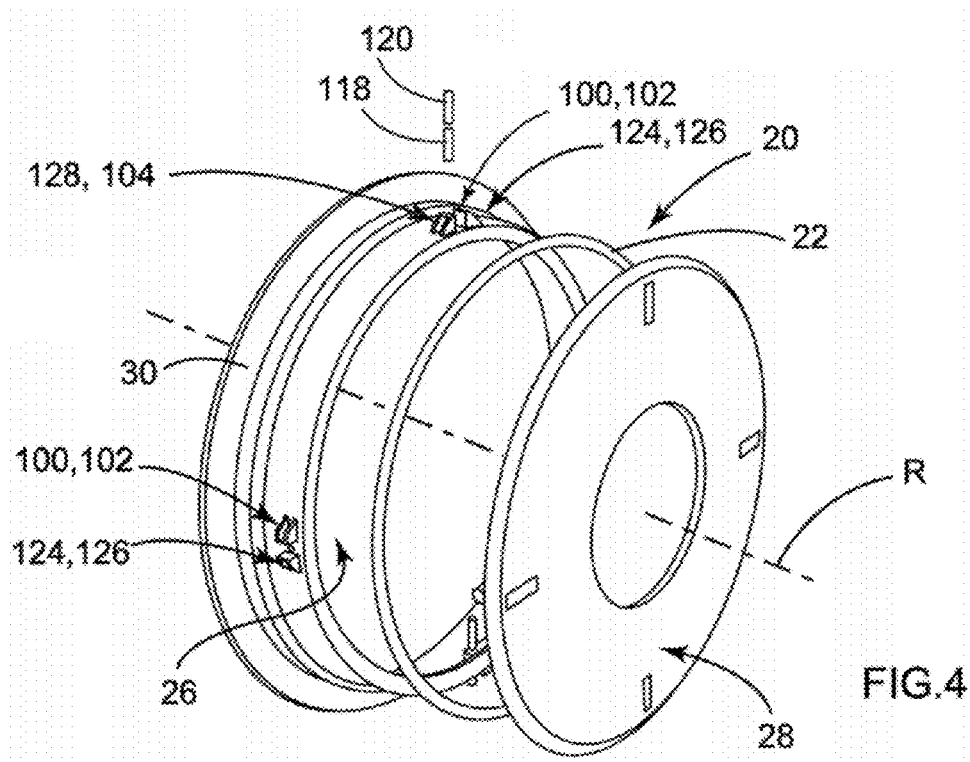
FIG. 4 is a general overview, showing an exploded perspective view of an embodiment of a container according to the invention where the peripheral envelope is not shown.

FIG. 4 shows more details of an embodiment of a container intended to be associated with the leaktight joining device of the invention.

The peripheral envelope of the container 20 is not shown in this illustration, however.

As indicated above, this container 20 is intended for the transport and the aseptic transfer of biopharmaceutical products to or from a chamber 10 equipped with the leaktight joining device 40 of the invention.

For that purpose, the container 20 comprises the annular flange 30 delimiting the annular opening 26, the removable cover 28 adapted for sealing the opening 26 of the annular flange 30, and the peripheral envelope integral with the annular flange 30 and delimiting the enclosed inside space 24 for containing the biopharmaceutical products. In this manner, when closed by the removable cover 28, the container 20 is sealed, preventing any leakage or any introduction of material into the inside space 24. The container 20 may be rigid or flexible and reusable or disposable, depending on the case. By way of example and in no way limiting, it may be a container 20 of any size, such as a bag, a sleeve, a vessel, a bioreactor, a spout, etc.

The container 20 also comprises built-in temporary clamping means 100.

These built-in temporary clamping means 100 are arranged on an outer peripheral edge of the annular flange 30 in a manner that allows temporarily clamping the container 20 by axially locking it in place on the outside face of the peripheral wall 10 of the chamber 10 via the actuation of the leaktight joining device 40.

More particularly, according to the embodiment of FIG. 4, the built-in temporary clamping means 100 comprise at least one built-in functional arrangement for temporary clamping 102 formed by at least one lug 104, preferably two lugs 104, having a built-in functional surface for axial clamping 106 adapted to abut against the stationary functional surface for axial clamping 56 of the leaktight joining device 40. These lugs 104, which can be positioned between the outer face of the peripheral wall 12 of the chamber 10 and the stationary functional surface for axial clamping 56 of the leaktight joining device 40 by first passing through one of the insertion openings 58 for the leaktight joining device 40, allow preventing axial movement of the container 20 relative to the chamber 10.

When the container 20 is clamped against the chamber 10, the removable cover 28 of the container 20 remains sealingly fixed—magnetically or by other means—against the removable door 108 of the chamber 10. In this manner, the outside space contained between the removable cover 28 and the removable door 18 cannot leak during the aseptic transfer.

The container 20 also comprises built-in locking/unlocking means 110 for holding the removable cover 28 on the annular flange 30.

These built-in locking/unlocking means 110—their structure is detailed below—have the function of maintaining the container 20 into three distinct positions. The first position is referred to as the initial locking position because the locking/unlocking means 110 prevent relative movement of the removable cover 28 with respect to the annular flange 30. The second position, referred to as the intermediate unlocking position, occurs when the annular flange 30 of the container 20 is clamped axially against the peripheral wall 12 of the chamber 10 and allows relative movement of the removable cover 28 with respect to the annular flange 30. The third position, referred to as the final locking position, is assumed to take place after the aseptic transfer of biopharmaceutical products between the container 20 and the chamber 10, and once again prevents, reversibly or irreversibly, the relative movement of the removable cover 28 with respect to the annular flange 30.

To ensure this transition from the initial locking position to the intermediate unlocking position and then to the final locking position, the built-in locking/unlocking means 110 according to the embodiment of FIG. 4 include four built-in functional arrangements for locking/unlocking 112 regularly distributed around the annular flange 28 of the cover 30.

Each built-in functional arrangement for locking/unlocking 112 comprises a through-housing 114 formed in the annular flange 30 and a blind housing 116 formed in the removable cover 28 of the container 20 and in the extension of the through-housing 114.

Each built-in functional arrangement for locking/unlocking 112 also comprises a pin at an inner radial position 118 and a pin at an outer radial position 120. In the embodiment of FIG. 4, these two pins at an inner 118 and outer 120 radial position have an elongated cylindrical body allowing them to be introduced and moved within the blind housing 116 formed in the removable cover 28 and within the through-housing 114 arranged in the annular flange 30. It should be noted that the dimensional characteristics and the properties of the outer surface of these inner 118 and outer 120 pins are such that these pins can only be moved within the blind housing 116 and the through-housing 114 by gravity. In addition, these inner 118 and outer 120 pins could have a different body shape—for example, parallelepipedal—to achieve the same result.

In the embodiment of FIG. 4, the through-housing 114, the blind housing 116, the pin at an inner radial position 118, and the pin 120 at an outer radial position, are coaxial and are aligned in a radial direction relative to the annular flange 30. More specifically, according to this embodiment, these elements extend in a substantially radial direction, oriented towards the geometric axis of rotation R. However, in an alternative embodiment, said through-housing 114, blind housing 116, pin at an inner radial position 118, and pin at an outer radial position 120 could be oriented in a slightly inclined direction forming an angle α which respect to a radial direction relative to the annular flange 30.

In the embodiment of FIG. 4, the blind housing 116 is flush with the through-housing 114, but it is also possible to have a gap between the blind housing 116 and the through-housing 114 without this affecting the containment and manipulation of the container 20.

Figure 5A:
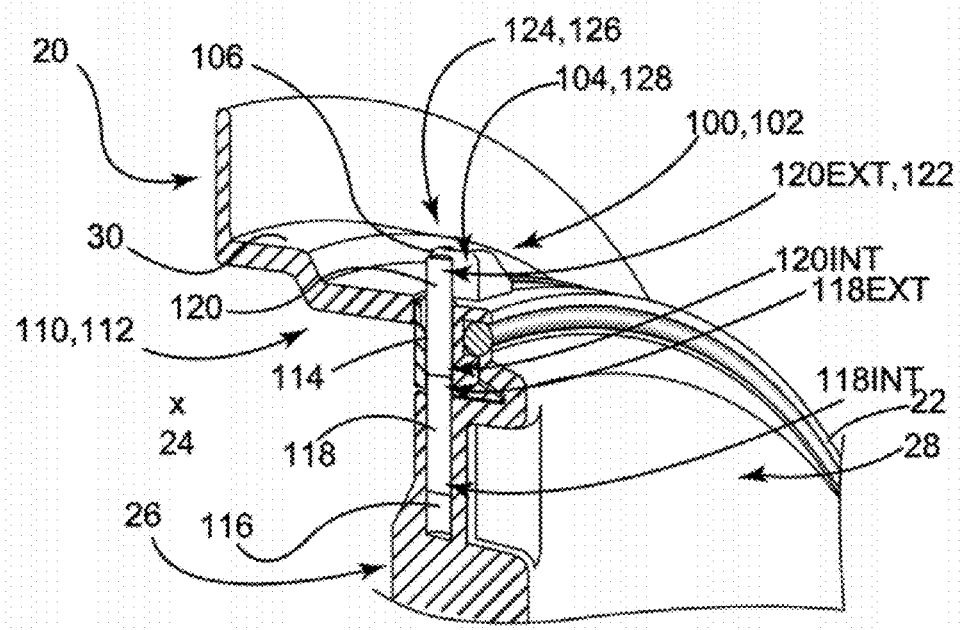
FIG. 5a is a cross-sectional detail view, showing a portion of the container of FIG. 4 in an initial locking position.

When the container 20 is in the initial locking position, as shown in FIG. 5a, the pin at an inner radial position 118 has an internal functional portion for initial locking $118_{INT}$ arranged in the blind housing 116 of the removable cover 28 and an external functional portion for initial locking $118_{EXT}$ arranged in the through-housing 114 of the annular flange 30. Thus, the pin at an inner radial position 118 prevents the relative movement of the removable cover 28 with respect to the annular flange 30.

Further, in this same initial locking position, the pin at an outer radial position 120 is at least partially arranged in the through-housing 114 of the annular flange 30. In a first embodiment (shown in FIG. 5a), the pin at an outer radial position 120 can then have a functional end portion at an outer radial position 122 that is completely outside the through-housing 114. This facilitates access to this functional end portion 122 by the stationary unlocking means 60 or locking means 70. In a second embodiment (not shown), the pin at an outer radial position 120 may alternatively have a functional end portion at an outer radial position 122 which is flush with the outer end opening of the through-housing 114. Access to this functional end portion 122 by the stationary unlocking means 60 or locking means 70 then remains relatively easy but the risk inadvertently moving the outer pin 120 is reduced. Lastly, according to a third embodiment (not shown), said pin at an outer radial position 120 may have a functional end portion at an outer radial position 122 which is entirely housed within the through-housing 114. In this manner, it is virtually impossible to manipulate the outer pin 120 without using a specific tool.

Figure 5B:
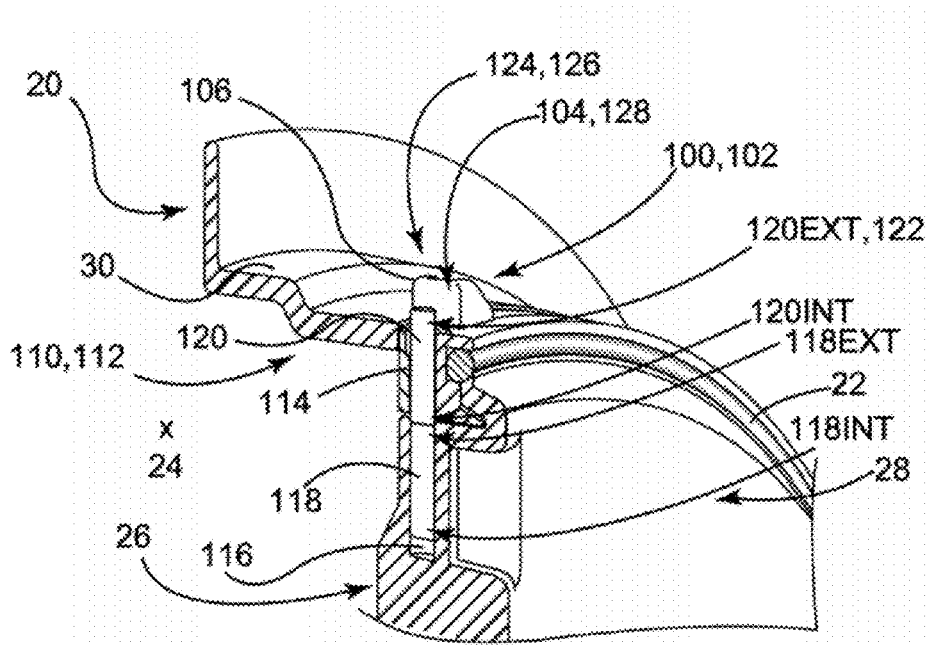
FIG. 5b is a cross-sectional detail view, showing a portion of the container of FIG. 4 in an intermediate unlocking position.

When the container 20 is in the intermediate unlocking position, as shown in FIG. 5b, the pin at an inner radial position 118 is at least partially arranged within the blind housing 116 of the removable cover 28 and is completely outside the through-housing 114 of the annular flange 30. The pin at an inner radial position 118 then no longer prevents the relative movement of the annular flange 30 and of the removable cover 28 of the container 20.

In this intermediate unlocking position, the pin at an outer radial position 120 still is at least partially arranged in the through-housing 114 of the annular flange 30 and is completely outside the blind housing 116 of the removable cover 28. The pin at an outer radial position 120 thus has no more effect than the pin at an inner radial position 118 on the relative movement of the removable cover 28 with respect to the annular flange 30, and they can therefore be separated to allow the aseptic transfer of biopharmaceutical products.

Similarly to the above, the functional end portion at an outer radial position 122 of said pin at an outer radial position 120 may either be completely outside the through-housing 114, or flush with the outer end opening of the through-housing 114, or be housed entirely within said through-housing 114.

Figure 5C:
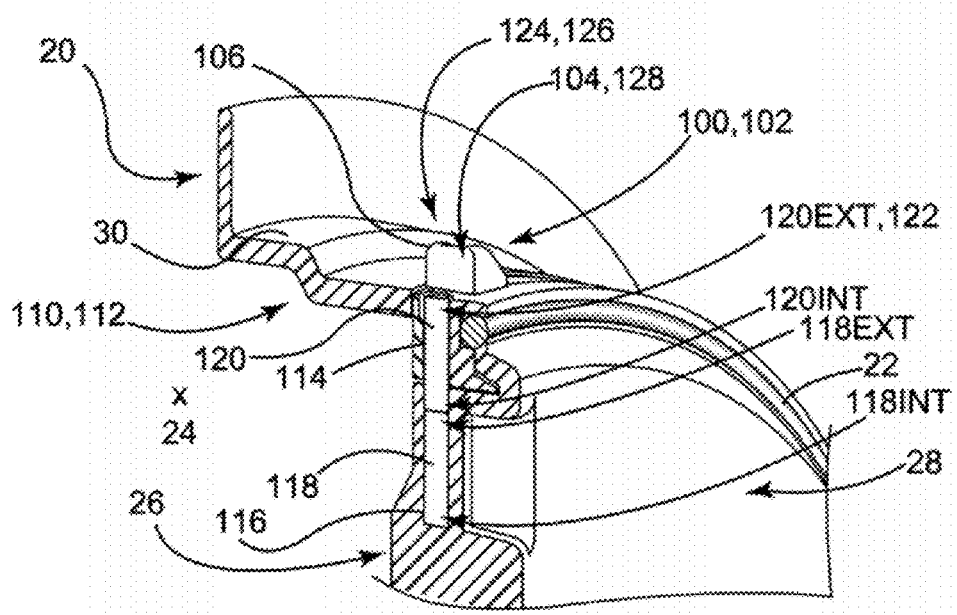
FIG. 5c is a cross-sectional detail view, showing a portion of the container of FIG. 4 in a final locking position.

Finally, to place the container 20 in the final locking position, as shown in FIG. 5c, it is first necessary to replace the removable cover 28 against the annular flange 30 and then place the built-in functional arrangement for locking/unlocking 112 in the appropriate position.

More particularly, in this position, the pin at an inner radial position 118 is positioned entirely within the blind housing 116 of the removable cover 28, while the pin at an outer radial position 120 has an internal functional portion for final locking $120_{INT}$ arranged in the blind housing 116 of the removable cover 28 and an external functional portion for final locking $120_{EXT}$ arranged in the through-housing 114 of the annular flange 30. Therefore, the blind housing 116 of the removable cover 28 has a length sufficient to accommodate the pin at an inner radial position 118 on the one hand, and the internal functional portion for final locking $120_{INT}$ on the other hand. Thus, the pin at an outer radial position 120 prevents the relative movement of the removable cover 28 with respect to the annular flange 30.

Once again, the functional end portion at an outer radial position 122 of said pin at an outer radial position 120 can then be completely outside the through-housing 114 in order to facilitate any subsequent reopening of the container 20.

Conversely, said functional end portion at an outer radial position 122 may be flush with the outer end opening of the through-housing 114 or may be housed entirely within said through-housing 114 to limit the subsequent risk of opening the container 20.

Such use of pins at inner 118 and outer 120 radial positions to place the container in the initial locking, intermediate unlocking, and final locking positions makes it possible to have only one blind housing 116 and through-housing 114 in the removable cover 28 and the annular flange 30 per built-in functional arrangement for locking/unlocking 112, which limits the risks of contamination due to production defects. In addition, manipulation of the locking/unlocking means 110 is facilitated, as it is sufficient to move the inner 118 and outer 120 pins in a single direction in order to transition the container 20 successively from the initial position locking position to the intermediate unlocking position and then to the final locking position. The construction and operation of the leaktight joining device are thus simplified.

It should be noted that in the embodiment of FIG. 4, the pins at inner 118 and outer 120 radial positions have identical lengths, which simplifies the production and assembly of the inner 118 and outer 120 pins on the container as it is then no longer necessary to distinguish the pins according to their dimensions. Alternatively, these pins at inner 118 and outer 120 radial positions could have different lengths.

It should also be noted that the through-housing 114 and the pin at an outer radial position 120 have lengths such that, when the built-in locking/unlocking means 110 are in the provisional unlocking position, the pin at an outer radial position 120 has a functional end portion 122 at an outer radial position which is completely outside the through-housing 114. This facilitates the operation carried out by the stationary locking means 70 for transitioning the container 20 from the intermediate unlocking position to the final locking position because the pin at an outer radial position 120 is accessible without the radially movable pushing element 78 having to be moved all the way to the inside of the through-housing 114.

However, the lengths of the pin at an outer radial position 120 and of the through-housing 114 are such that, when the built-in locking/unlocking means 110 are in the final locking position, said pin at an outer radial position 120 has a functional end portion 120 at an outer radial position that is housed within the through-housing. When the container is placed in the final locking position, it then becomes complex and impractical without a suitable gripping tool to grasp the pin at an outer radial position 120. This raises the level of security related to the fluid-tightness of the container 20 in the final locking position.

To this end, it would also be possible to integrate complementary protection and warning means—formed for example by complementary abutments or any similar element—on the pin at an outer radial position 120 and on the through-housing 114, preventing the removal of the pin at an outer radial position 120 from the through-housing 114 after the container 20 has been placed in the final locking position and causing the destruction of a portion of the annular flange 30 in the event of such removal.

Alternatively (not shown), it is also possible for the lengths of the pin at an outer radial position 120 and of the through-housing 114 to be such that, when the built-in locking/unlocking means 110 are in the final locking position, said pin at an outer radial position 120 has a functional end portion at an outer radial position which is completely outside the through-housing.

Such an embodiment would, however, facilitate the removal of the pin at an outer radial position 120 from the through-housing 114 and would proviode a container that is reusable after being placed in the final locking position.

According to the embodiment of FIG. 4, the container 20 also comprises built-in isolation and protection means 124.

The built-in isolation and protection means 124 are arranged on an outer peripheral portion of the annular flange 30 so as prevent inadvertent manipulation of the built-in locking/unlocking means supported by the annular flange 30.

In one embodiment, the built-in isolation and protection means 124 include four built-in functional arrangements for isolation and protection 126 placed around four through-housings 114 so as to prevent inadvertent or deliberate manipulation of the pin at an outer radial position 120 when said pin is not fully inserted into the through-housing 118 of the annular flange 30.

Each built-in functional arrangement for isolation and protection 126 is based on two lugs 128, arranged around or on either side of the through-housing 114. In this embodiment, the lugs 128 have radial dimensions such that, in the provisional locking position, the pin at an outer radial position 120 does not extend beyond the lugs 128 that are part of the isolation and protection means.

However, in an alternative or additional embodiment, the built-in functional arrangement for isolation and protection 62 could be based on a bore formed in the annular flange 30, radially oriented and having a diameter greater than the diameter of the through-housing 114. Such an embodiment would prevent access to the outer pin 120 while maintaining the space around this outer pin 120 in order to avoid complicating the operation of moving said pin by the stationary unlocking means 60 and locking means 70.

It should be noted that, in the embodiment of FIG. 4, the lugs 104 forming the built-in temporary clamping means 102 and the lugs 128 forming the built-in isolation and protection means 124 are the same. These lugs 104, 108 therefore have, on the one hand, a built-in functional surface for axial clamping 56 ensuring the clamping of the container against the peripheral wall 12 of the chamber 10, and on the other hand, a shape which protects and isolates the outer pin 120 when it is only partially inserted into the through-housing 114. Such an embodiment can reduce production costs and simplify the annular flange 30 by limiting the number of lugs to be created on the outer peripheral edge of the annular flange 30.

However, it would also be conceivable to use built-in temporary clamping means 102 and built-in isolation and protection means 124 that are structurally and functionally independent of each other, for example using some lugs 104 for the axial clamping and other different lugs for the isolation and protection of the outer pins 120.

It should be noted that similarly to the above, the built-in temporary clamping means 100 are arranged so as to index the position of the container 20 relative to the other stationary means that are part of the leaktight joining device 40. This accumulation of functional arrangements on the annular functional ring gear 42 allows completing a manipulation cycle of the container with only a 1/n revolution of the annular functional ring gear 42. In the current case, the embodiment comprises four distinct functional arrangements distributed evenly around the annular functional ring gear 42, although it would be possible to include fewer—one, two, or three—or to include more.

Figure 6:
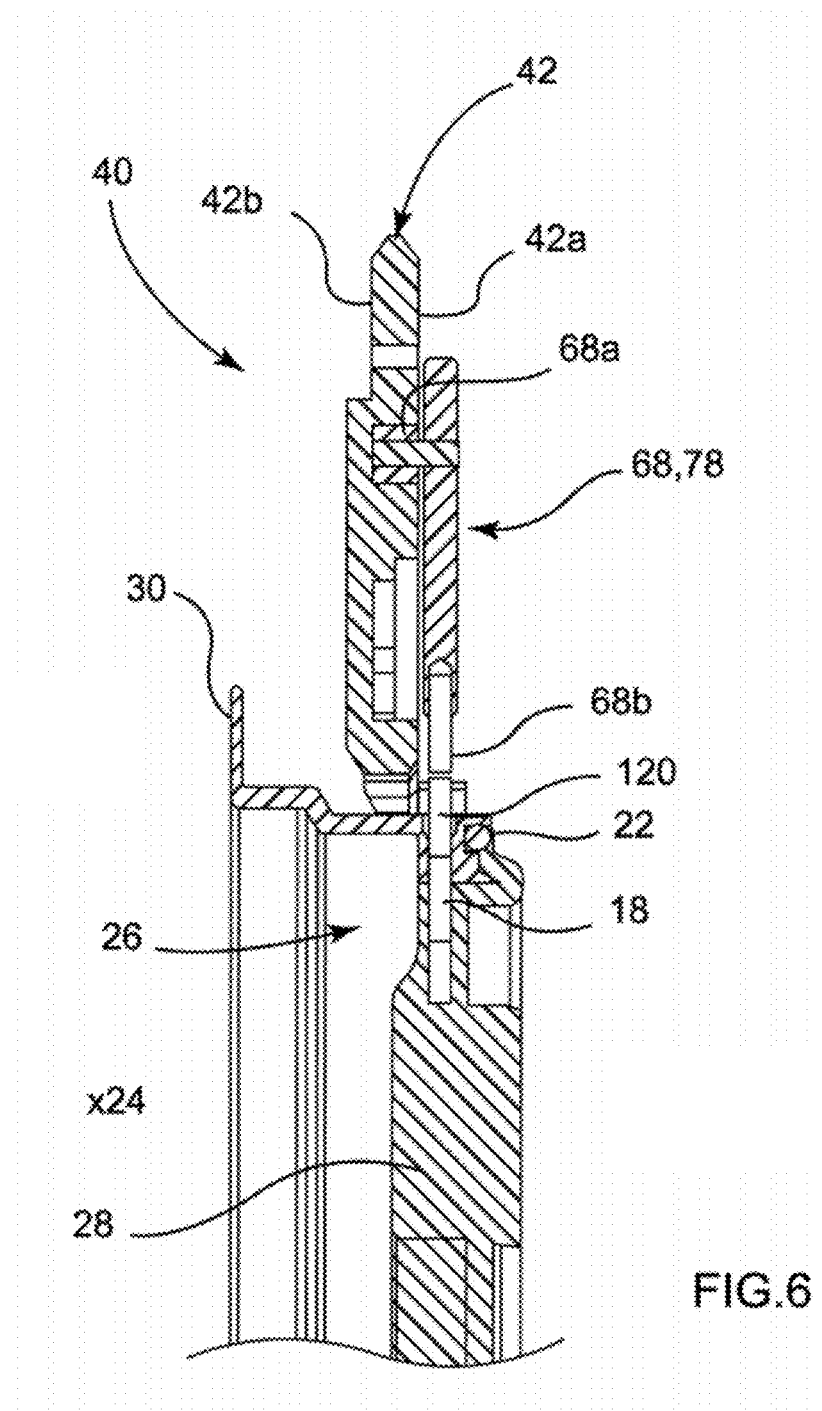
FIG. 6 is a cross-sectional detailed representation of an assembly comprising a closed chamber, a leaktight joining device, and a container according to the invention associated with the leaktight joining device and in the initial locking position.

The implementation of the aseptic transfer method of the invention will now be described in detail, with reference to FIG. 6.

This aseptic transfer method first consists of having a closed chamber 10 as described above and supporting a leaktight joining device 40 of the invention. Then this aseptic transfer method consists of having a container 20 in the initial locking position as described above.

The aseptic transfer method next involves placing the container 20 against the peripheral wall 12 of the chamber 10, introducing the lugs 104 that are part of the built-in functional arrangements for temporary clamping 102 through the insertion openings 58 that are part of the stationary temporary clamping means 50.

By doing so, the annular flange 30 of the container 20 comes into position against the peripheral wall 12 of the chamber 10 and the removable cover 28—at least partially formed of ferrite—is sealingly held against the outer face of the removable door 18—at least partially magnetized.

The aseptic transfer method then consists of generating the clockwise rotation of the annular functional ring gear 42 so that the functional clamping ring portions 54 are positioned facing the lugs 104 forming the built-in temporary clamping means and trap these lugs 104 between the peripheral wall 12 of the chamber 10 and the functional surfaces for axially clamping 56.

The container 20 is thus held in position by the leaktight joining device 40 against the peripheral wall 12 of the chamber 10.

The aseptic transfer method then consists of generating the clockwise rotation of the annular functional ring gear 42 to actuate the stationary unlocking means 60. More particularly, the clockwise rotation of this annular functional ring gear 42 generates a movement of the radially movable pushing element 68 due to the change in radial position of the roller 68a in the guideway 66. The activation pin 68b then lowers, at the same time pushing the pin at an outer radial position 120 and the pin at an inner radial position 118.

Following this operation, the pin at an inner radial position 118 is then arranged in the blind housing 116 of the removable cover 28 and is completely outside the through-housing 114 of the annular flange 30, and the pin at an outer radial position 120 is arranged in the through-housing 114 of the annular flange 30 and is completely outside the blind housing 116 of the removable cover 28. The container 20 is thus in the intermediate unlocking position and the relative movement of the removable cover 28 with respect to the annular flange 30 is possible.

The aseptic transfer method also consists of, simultaneously with or successively to the preceding step, generating the clockwise rotation of the annular functional ring gear 42 to actuate the stationary retention/release means 80 in order to release the removable door 18 of the chamber 10.

To this end, the functional ring portions forming gear teeth 84—which are rotated with the annular functional ring gear 42—engage with the drive shaft 86 and therefore with the retention member 88 so that the latter no longer covers the outer face of the removable door 18 of the chamber 10. The removable door 18 can then be operated freely.

The aseptic transfer method then consists of using the stationary operating means 90 to move the removable door 18 of the chamber 10 and the removable cover of the container in order to free the annular openings 16, 26 of the chamber 10 and of the container 20.

To do this, the stationary operating means 90—which may be actuated by the annular functional ring gear 42 or by a motor controlled by the position of said annular functional ring gear 42—first drive the removable door 18 of the chamber 10 in a horizontal translation and then in a rotation about a horizontal axis.

As the container 20 is in the intermediate unlocking position, the removable cover 28 can be moved relative to the annular flange 30 and can follow the movements of the removable door 18 of the chamber 10 due to the magnetic force connecting them together. Thus, the chamber 10 and the container 20 are open to each other while being hermetically isolated from the outside environment.

The aseptic transfer of biopharmaceutical products between the container 20 and the chamber 10 can then occur.

The aseptic transfer method then consists of once again using the stationary operating means 90 to seal closed the annular openings 16, 26 of the chamber 10 and of the container 20.

As above, the stationary operating means 90 cause the removable door of the chamber 10 and the removable cover of the container 20 to move rotationally about a horizontal axis and then in a horizontal translation in order to return them to the same position as before.

The chamber 10 is then once again sealed by the removable door 18, relative to the outside and to the container 10. Symmetrically, the container 20 is sealed by the removable cover, relative to the outside and to the chamber 10.

The aseptic transfer method then consists of generating the clockwise rotation of the annular functional ring gear 42 to actuate the stationary retention/release means 80 in order to prevent movement of the removable door 18 of the chamber 10.

For this purpose, the functional ring portions forming gear teeth 84—which rotate with the annular functional ring gear 42—engage the drive shaft 86 and thus the retention member 88, so that said retention member once again covers the outer face of the removable door 18 of the chamber 10. The removable door 18 can then no longer be operated freely.

The aseptic transfer method consists, simultaneously with or successively to the previous step, of generating the clockwise rotation of the annular functional ring gear 42 in order to actuate the stationary locking means 70. More particularly, the clockwise rotation of this annular functional ring gear 42 generates a movement of the radially movable pushing element 78 due to the change in radial position of the roller 68a in the guideway 76. The activation pin 68b then lowers, at the same time pushing the pin at an outer radial position 120 and the pin at an inner radial position 118.

Following this operation, the pin at an inner radial position 118 is arranged within the blind housing 116 of the removable cover 28 while the pin at an outer radial position 120 has an internal functional portion for final locking $120_{INT}$ arranged within the blind housing 116 of the removable cover 28 and an external functional portion for final locking $120_{EXT}$ arranged within the through-housing 114 of the annular flange 30. Relative movement of the removable cover 28 with respect to the annular flange 30 is rendered impossible and the container is then in the final locking position.

The aseptic transfer method then consists of generating the clockwise rotation of the annular functional ring gear 42 so that the functional ring portions acting as temporary clamp 54 are positioned so the insertion openings 58 are facing the lugs 104 forming the built-in temporary clamping means and free them.

The container 20 in the final locking position can thus be freely removed from the leaktight joining device 40.

The invention claimed is:

1. A leaktight joining device intended for ensuring the aseptic transfer of a biopharmaceutical product between a chamber equipped with a removable door and a container equipped a removable cover, comprising:
    stationary temporary clamp able to keep the container clamped against the chamber so that the removable cover of said container is sealingly held against the removable door of said chamber;
    a stationary unlocking device able to transition the container from an initial locking position where the removable cover seals the container to an intermediate unlocking position where the removable cover is disengaged from the container and is sealingly held against the removable door of the chamber so as to ensure an aseptic communication between said container and said chamber;
    a stationary locking device able to transition the container from the intermediate unlocking position to a final locking position where said removable cover once again seals the container;
    an annular functional ring gear able to rotate about a geometric axis of rotation so as to actuate the stationary unlocking device and the stationary locking device of the container;
    wherein the stationary temporary clamp, stationary unlocking device, and stationary locking device are mechanically linked to the annular functional ring gear and are arranged so that a one-way rotation of said annular functional ring gear about the geometric axis of rotation successively causes the actuation of the stationary temporary clamp which ensures that the container is held in position against the chamber, then simultaneously or successively the actuation of the stationary unlocking device which ensures the transition to the intermediate unlocking position of the container, then the actuation of the stationary locking device of the container which ensures the transition to the final locking position of the container, and the actuation of the stationary temporary clamp of the container in order to release the container.

2. The leaktight joining device according to claim 1, further comprising a stationary retention/release device able to disable/enable the opening of the removable door of the chamber and mechanically linked to the annular functional ring gear such that the one-way rotation of the annular functional ring gear about the geometric axis of rotation successively causes the actuation of the stationary temporary clamp which ensures that the container is held in position against the chamber, then simultaneously or successively the actuation of the stationary unlocking device which ensures the transition to the intermediate unlocking position of the container and the actuation of the stationary retention/release device which ensures the release of the removable door of the chamber, then the actuation of the stationary locking device of the container which ensures the transition to the final locking position of the container, then simultaneously or successively the actuation of the stationary retention/release device which ensures the retention of the removable door of the chamber and the actuation of the stationary locking device which ensures the transition to the final locking position of the container, then the actuation of the stationary temporary clamp in order to release the container relative to the chamber.

3. The leaktight joining device according to claim 2, wherein the stationary retention/release device comprise at least one stationary functional arrangement for retention/release formed by a functional ring portion forming gear teeth and a retention member able to engage with the functional ring portion forming gear teeth such that, during the one-way rotation of the annular functional ring gear, the retention member moves from a retention position where a covering portion prevents the removable door of the chamber from opening, to a release position where the covering portion no longer prevents the removable door of the chamber from opening.

4. The leaktight joining device according to claim 1, wherein the stationary unlocking device comprises at least one stationary functional unlocking arrangement formed by a functional ring portion forming an inward- and/or outward-facing radial cam and a radially movable pushing element cooperating with the functional ring portion forming the radial cam so that, during the one-way rotation of the annular functional ring gear to the intermediate unlocking position, the pushing element is moved and causes the container to transition from the initial locking position to the intermediate unlocking position.

5. The leaktight joining device according to claim 1, wherein the stationary locking device comprises at least one stationary functional locking arrangement formed by a functional ring portion forming an inward- and/or outward-facing radial cam, and a radially movable pushing element cooperating with the functional ring portion forming the radial cam such that, during the one-way rotation of the annular functional ring gear to the final locking position, the pushing element is moved and causes the removable cover of the container to transition from the intermediate unlocking position to the final locking position.

6. The leaktight joining device according to claim 4,
    wherein the stationary locking device comprises at least one stationary functional locking arrangement formed by a functional ring portion forming an inward- and/or outward-facing radial cam, and a radially movable pushing element cooperating with the functional ring portion forming the radial cam such that, during the one-way rotation of the annular functional ring gear to the final locking position, the pushing element is moved and causes the removable cover of the container to transition from the intermediate unlocking position to the final locking position, and
    wherein the functional ring portion forming the radial cam of the stationary locking device and/or unlocking device is formed by a guideway arranged in the annular functional ring gear, and the radially movable pushing element of said stationary locking device and/or unlocking device comprises a roller arranged in the guideway so that rotation of the annular functional ring gear generates a radial movement of the roller which causes the corresponding movement of an activation pin.

7. The leaktight joining device according to claim 4,
    Wherein the stationary locking device comprise at least one stationary functional locking arrangement formed by a functional ring portion forming an inward- and/or outward-facing radial cam, and a radially movable pushing element cooperating with the functional ring portion forming the radial cam such that, during the one-way rotation of the annular functional ring gear to a final locking position, the pushing element is moved and causes the removable cover of the container to transition from the intermediate unlocking position to the final locking position, and wherein the stationary functional unlocking arrangement and the stationary functional locking arrangement are composed of the same radially movable pushing element.

8. The leaktight joining device according to claim 7, wherein the functional ring portion forming a radial cam of the stationary functional locking arrangement is arranged in an extension of the functional ring portion forming the inward- and/or outward-facing radial cam of the stationary functional unlocking arrangement, considering the one-way direction of rotation of the annular functional ring gear.

9. The leaktight joining device according to claim 8, wherein the ring portions forming the radial cams of the stationary functional locking arrangement and of the stationary functional unlocking arrangement are formed by a continuous guideway arranged in the annular functional ring gear, and the radially movable pushing element comprises a roller arranged in the continuous guideway such that the rotation of the annular functional ring gear generates radial movement of the roller which results in the corresponding displacement of an activation pin.

10. The leaktight joining device according to claim 1, wherein the stationary temporary clamp comprise at least one stationary functional arrangement for temporary clamping implemented based on a functional clamping ring portion having, on the one hand, a functional surface for axial clamping and, on the other hand, an insertion opening for a built-in complementary clamp arranged on a portion of the outer periphery of the container.

11. The leaktight joining device according to claim 10, wherein the functional clamping ring portion is implemented on an inner peripheral edge of the annular functional ring gear.

12. The leaktight joining device according to claim 1, comprising a stationary operating device for the removable door of the chamber, able to open and seal closed the removable door the chamber.

13. The leaktight joining device according to claim 12, wherein the stationary operating device for the removable door of the chamber are mechanically driven by the annular functional ring gear.

14. The leaktight joining device according to claim 12, wherein the stationary operating device for the removable door of the chamber are driven by a motor controlled by the movements of the annular functional ring gear.

15. The leaktight joining device according to claim 12, wherein the stationary operating device for the removable door of the chamber are adapted to move the removable door of the chamber first in an axial direction, then in a direction substantially perpendicular to the axial direction so that the door does not obstruct the passage of the biopharmaceutical product.

16. The leaktight joining device according to claim 1, wherein the annular functional ring gear, the stationary temporary clamp, the stationary unlocking device, and the stationary locking device is positioned outside the chamber.

17. The leaktight joining device according to claim 3, wherein, firstly, the annular functional ring gear, the stationary temporary clamp, the stationary unlocking device, the stationary locking device, and the functional ring portion forming gear teeth of the stationary functional arrangement for retention/release are positioned outside the chamber, secondly, the retention member of said stationary functional arrangement for retention/release is positioned inside the chamber, and thirdly, said retention member is driven by a drive shaft which passes through the peripheral wall of the chamber.

18. The leaktight joining device according to claim 1, wherein the stationary temporary clamp, the stationary unlocking device, and the stationary locking device respectively comprise n stationary functional arrangement(s) for temporary clamping, n stationary functional unlocking arrangement(s), n stationary functional locking arrangement(s), with n greater than or equal to 1, so that with each rotational movement of the annular functional ring gear in the one-way direction corresponding to 1/n complete revolutions there is the corresponding successive actuation of the stationary temporary clamp of the container to hold the container in position against the chamber, of the stationary unlocking device of the container to ensure the transition to the intermediate unlocking position of the container, of the stationary locking device of the container to ensure the transition to the final locking position of the container, and of the stationary temporary clamp of the container to ensure the release of said container.

19. The leaktight joining device according to claim 18, wherein n is equal to 3 or 4.

20. An assembly comprising a chamber and a leaktight joining device specially intended for association with a single-use container equipped with a removable cover in order to perform the aseptic transfer of a biopharmaceutical product between the chamber and the container, wherein the chamber comprises an enclosed peripheral wall having an annular opening that is sealed by a removable door, and wherein the leaktight joining device is implemented according to claim 1.

21. The assembly according to claim 20, further comprising a single-use container equipped with a removable cover.

22. The assembly according to claim 21, wherein the single-use container is specially intended for the transport and the aseptic transfer of a product belonging to the biopharmaceutical field and comprises:
an annular flange delimiting an opening;
a removable cover adapted for sealing the opening of the annular flange;
a built-in device for locking/unlocking the removable cover on the annular flange; and
a peripheral envelope integral with the annular flange and delimiting an enclosed inside space adapted for receiving products belonging to the biopharmaceutical field;
wherein the built-in locking/unlocking device comprises at least one built-in functional locking/unlocking arrangement formed by a through-housing formed in the annular flange and a blind housing formed in the removable cover and in an extension of the through-housing when the removable cover seals the opening of the annular flange, and by a pin at an inner radial position and a pin at an outer radial position both capable of being introduced and moved within the blind housing of the removable cover and the through-housing of the annular flange;
the container being able to be in an initial locking position where the pin at the inner radial position has an internal functional locking portion arranged in the blind housing of the removable cover and an external functional locking portion arranged in the through-housing of the annular flange so as to prevent the relative movement of the removable cover with respect to the annular flange, and the pin at the outer radial position is at least partially arranged in the through-housing of the annular flange;

the container being able to be in an intermediate unlocking position where the pin at the inner radial position is at least partially arranged in the blind housing of the removable cover and is completely outside the through-housing of the annular flange, and the pin at the outer radial position is at least partially arranged in the through-housing of the annular flange and is completely outside the blind housing of the removable cover so as to allow the relative movement of the removable cover with respect to the annular flange;

the container being able to be in a final locking position where the pin at the inner radial position is arranged in the blind housing of the removable cover, and the pin at the outer radial position has an internal functional portion for final locking arranged in the blind housing of the removable cover and an external functional portion for final locking arranged in the through-housing of the annular flange so as to prevent the relative movement of the removable cover with respect to the annular flange.

23. An aseptic transfer method, intended for the aseptic transfer of a biopharmaceutical product between a container and a chamber which are part of an assembly according to claim 20, comprising successive steps of:

providing the chamber, the leaktight joining device, and the container;

positioning the container against the peripheral wall (12) of the chamber;

generating an axial clamping of the annular flange of the container against the peripheral wall of the chamber by a one-way rotation of the annular functional ring gear;

generating the transition of the container from the initial locking position to the intermediate unlocking position by one-way rotation of the annular functional ring gear;

simultaneously opening the removable door of the chamber and the removable cover of the container, the removable cover being sealingly attached against the removable gate;

aseptically transferring one or more biopharmaceutical product(s) between the container and the chamber;

simultaneously closing the removable door of the chamber and the removable cover of the container, the removable cover being sealingly attached against the removable door;

generating the transition of the container from the intermediate unlocking position to the final locking position by one-way rotation of the annular functional ring gear;

generating the axial unclamping of the annular flange of the container with respect to the peripheral wall of the chamber by one-way rotation of the annular functional ring gear.

* * * * *